(12) United States Patent
Fushimi et al.

(10) Patent No.: US 7,371,883 B2
(45) Date of Patent: May 13, 2008

(54) CATALYTIC OXIDATION PROCESS

(75) Inventors: Rebecca Fushimi, O'Fallon, MO (US); Anne Mae Gaffney, West Chester, PA (US); John T. Gleaves, Foley, MO (US); Scott Han, Lawrenceville, NJ (US); Sergiy O. Shekhtman, Saint Louis, MO (US); Gregory S. Yablonsky, Saint Louis, MO (US)

(73) Assignee: Rohm and Haas Company, Philadelphia, PA (US)

( * ) Notice: Subject to any disclaimer, the term of this patent is extended or adjusted under 35 U.S.C. 154(b) by 216 days.

(21) Appl. No.: 11/102,414

(22) Filed: Apr. 8, 2005

(65) Prior Publication Data

US 2005/0261511 A1 Nov. 24, 2005

Related U.S. Application Data

(60) Provisional application No. 60/560,837, filed on Apr. 8, 2004.

(51) Int. Cl.
*C97C 253/00* (2006.01)
*C07C 51/16* (2006.01)

(52) U.S. Cl. ...................... 558/323; 562/549

(58) Field of Classification Search ............... None
See application file for complete search history.

(56) References Cited

U.S. PATENT DOCUMENTS

| | | | |
|---|---|---|---|
| 3,292,290 A | 12/1966 | Flint et al. | |
| 5,218,146 A | 6/1993 | Takata et al. | |
| 5,281,745 A | * 1/1994 | Ushikubo et al. | 558/319 |
| 6,383,978 B1 | 5/2002 | Bogan, Jr. | |
| 6,403,525 B1 | 6/2002 | Chaturvedi et al. | |
| 6,407,031 B1 | 6/2002 | Chaturvedi et al. | |
| 6,407,280 B1 | 6/2002 | Chaturvedi et al. | |
| 6,461,996 B2 | 10/2002 | Chaturvedi et al. | |
| 6,472,552 B1 | 10/2002 | Bogan, Jr. | |
| 6,504,053 B1 | 1/2003 | Chaturvedi et al. | |
| 6,589,907 B2 | 7/2003 | Chaturvedi et al. | |
| 6,624,111 B2 | 9/2003 | Chaturvedi et al. | |
| 6,642,174 B2 | * 11/2003 | Gaffney et al. | 502/311 |
| 6,646,158 B1 | 11/2003 | Khan et al. | |
| 6,693,059 B2 | 2/2004 | Lin | |

FOREIGN PATENT DOCUMENTS

EP 1074538 2/2001

OTHER PUBLICATIONS

Kerler et al, Catalysis Today, Partial Oxidation of Alkanes to Oxygenates in Supercritical Carbon Dioxide, 2000, 61, pp. 9-17.*
Kerler et al, Catalysis Letters, (VO)2P2O7 Catalyzed Partial Oxidation of Propane in Dense, CO2, 2002, 78(1-4), pp. 259-265.*
O.V. Krylov, et al. "The regularities in the interaction of alkanes with $CO_2$ on oxide catalysts", Catalysis Today 24 (1995) 371-375.

* cited by examiner

*Primary Examiner*—Paul A. Zucker
(74) *Attorney, Agent, or Firm*—Marcella Badner

(57) ABSTRACT

An improved single-step catalytic vapor phase (amm)oxidation process for the conversion of one or more $C_2$-$C_8$ alkanes to one or more oxidation products, including unsaturated carboxylic acids and unsaturated nitriles, whereby a higher yield of the oxidation products is achieved.

11 Claims, 1 Drawing Sheet

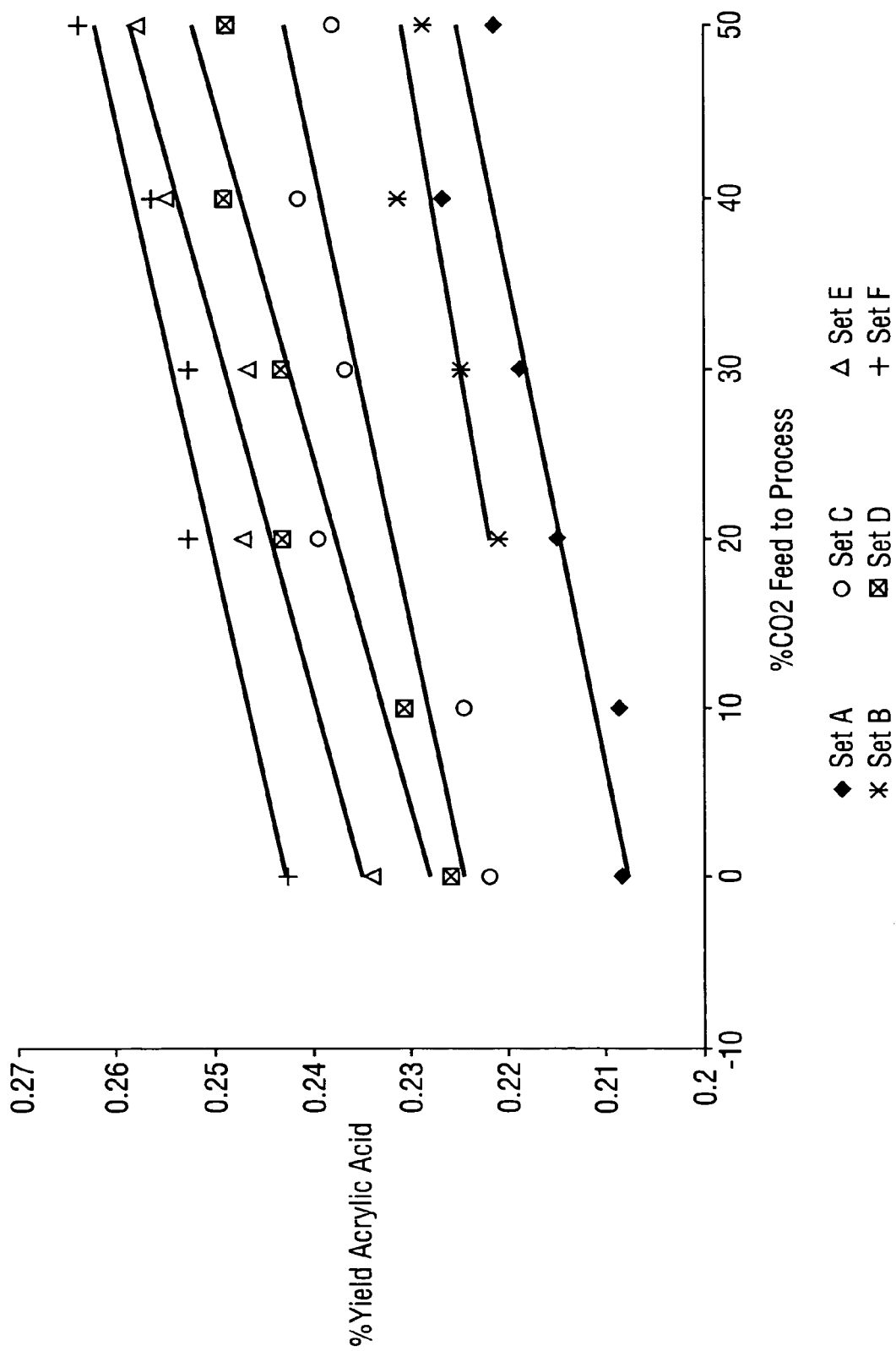

CATALYTIC OXIDATION PROCESS

CROSS REFERENCE TO RELATED PATENT APPLICATIONS

This is a non-provisional patent application of co-pending U.S. provisional patent application Ser. No. 60/560,837 filed Apr. 08, 2004.

FIELD OF THE INVENTION

The present invention relates to an improved single-step catalytic vapor phase (amm)oxidation process for the conversion of one or more $C_2$-$C_8$ alkanes to one or more oxidation products, including unsaturated carboxylic acids and unsaturated nitriles, whereby a higher yield of the oxidation products is achieved.

BACKGROUND OF THE INVENTION

Unsaturated carboxylic acids such as acrylic acid and methacrylic acid are industrially important as starting materials for various synthetic resins, coating materials and plasticizers. Nitriles, such as acrylonitrile and methacrylonitrile, are industrially important intermediates for the preparation of fibers, synthetic resins, synthetic rubbers, and the like. Such unsaturated carboxylic acids and nitriles can be produced by catalytic (amm)oxidation of lower (i.e., $C_2$-$C_8$) alkanes and alkenes, such as ethane, ethane, propane, propene, butane (including n- and iso-butane), butane (including n- and iso-butene) and pentane (including n- and iso-pentane) and pentane (including n- and iso-pentene).

For example, the currently practiced commercial process for the production of acrylic acid involves a two-step catalytic vapor phase oxidation reaction using an alkene, propene, as the hydrocarbon starting material. In the two-step oxidation reaction, propene is converted to acrolein over a suitable mixed metal oxide catalyst in the first step. In the second step, acrolein product from the first step is converted to acrylic acid using a second suitable mixed metal oxide catalyst. In most cases, the catalyst formulations are proprietary to the catalyst supplier, but the technology is well established. Furthermore, it is known to include additional starting materials, including additional reactants, such as molecular oxygen and/or steam, and inert materials, such as nitrogen and carbon dioxide, along with the hydrocarbon starting material that is fed to such two-step oxidation processes. See, for example, U.S. Pat. No. 5,218,146, which discloses a two-step catalytic vapor phase oxidation process for conversion of propene to acrylic acid. In the disclosure of U.S. Pat. No. 5,218,146, carbon dioxide is fed to the two-step oxidation process in an amount of from 3% to 50% by volume, based upon the total volume of the starting materials, which also include propene and molecular oxygen. There is, however, no correlation provided, expressly or implicitly, in U.S. Pat. No. 5,218,146 between the amount of carbon dioxide which is fed to the process and the yield of acrylic acid product.

The most popular method for producing nitriles is to subject an alkene (olefin), such as propene or isobutene, to a catalytic reaction with ammonia and oxygen in the presence of a suitable catalyst in a gaseous phase at a high temperature. There are various known catalysts suitable for conducting this reaction and, while many of the catalyst formulations are proprietary to the catalyst supplier, this technology is also well established. Furthermore, it is known to include additional starting materials, including additional reactants, such as molecular oxygen and/or steam, and inert materials, such as nitrogen and carbon dioxide, along with the hydrocarbon and ammonia starting materials that are fed to such two-step ammoxidation processes.

In view of the lower price of alkanes (for example, propane and isobutene) in comparison to alkenes (for example, propene and isobutene), attention has been drawn to the development of catalysts and processes for the production of unsaturated carboxylic acids and unsaturated nitrites in a single-step vapor phase (amm)oxidation process using the cheaper alkane as the hydrocarbon starting material. For example, catalysts capable of catalyzing the single-step oxidation of propane to acrylic acid in yields up to 52% have been developed and continue to be improved.

In addition, some refinements to the single-step oxidation process itself have been developed and further improvements to the single-step oxidation process continue to be sought and welcomed by industry. For example, it is known to include additional starting materials, including additional reactants, such as molecular oxygen and/or steam, as well as inert materials, such as nitrogen and carbon dioxide to act as diluents or heat moderators, along with the hydrocarbon starting material that is fed to the one-step oxidation process.

For example, U.S. Pat. No. 6,646,158 which states that carbon dioxide may be fed to the oxidation process in amounts greater than 5% by volume, based on the total volume of the feed gases, but no examples are provided that include feeding carbon dioxide to the disclosed process. Thus, carbon dioxide is not required for this process and no conclusions may be drawn from U.S. Pat. No. 6,646,158 regarding the efficacy of carbon dioxide as a diluent or heat moderator. In addition, U.S. Pat. No. 6,693,059 discloses the possibility of feeding a diluting gas, such as nitrogen, argon, helium or carbon dioxide, in an amount of from 0% to 20%, by volume, to a single-step oxidation process which converts propane to acrylic acid. This patent, however, is focused on the catalyst composition and activity and no examples are provided that include feeding carbon dioxide to the single-step oxidation process. O. V. Krylov et al., in "*The regularities in the interaction of alkanes with $CO_2$ on oxide catalysts*," Catalysis Today 24 (1995) 371-375, disclose the use of carbon dioxide as a non-traditional oxidant in the oxidation of methane, ethane and propane, but the products include only synthesis gases (hydrogen and carbon monoxide) and simple oxydehydrogenation products such as alkenes, without production of unsaturated carboxylic acids or nitrites. Thus, none of these prior disclosures explore or discuss the use of carbon dioxide as a feed component to single-step (amm)oxidation processes for increasing the production of (amm)oxidation products, including unsaturated carboxylic acids and nitrites.

Thus, the chemical industry would welcome further improvements to increase the yields of single-step (amm) oxidation processes for the conversion of one or more $C_2$ to $C_8$ alkanes to valuable (amm)oxidation products, including unsaturated carboxylic acids and nitrites.

SUMMARY OF THE INVENTION

The present invention provides a process for single-step catalytic vapor phase (amm)oxidation of one or more $C_2$-$C_8$ alkanes to produce one or more (amm)oxidation products, using one or more reaction zones, each of which comprises at least one catalyst capable of catalyzing the single-step vapor phase (amm)oxidation reaction. The inventive process comprises the steps of feeding the one or more $C_2$-$C_8$ alkanes to at least one of the one or more reaction zones; and feeding carbon dioxide to at least one of the one or more reaction zones simultaneously with the feeding of the one or more $C_2$-$C_8$ alkanes. The carbon dioxide may be fed in an amount of from 5 volume % to 60 volume %, and the one or more $C_2$-$C_8$ alkanes may be fed in an amount of from 3 volume % to 50 volume %, based upon the total volume of starting materials. The one or more (amm)oxidation products are selected from the group consisting of unsaturated carboxylic acids and unsaturated nitriles.

The at least one catalyst of the one or more reaction zones may comprise a mixed metal oxide having the empirical formula:

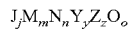

wherein J is at least one element selected from the group consisting of Mo and W, M is at least one element selected from the group consisting of V and Ce, N is at least one element selected from the group consisting of Te, Sb and Se, Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements; and wherein said catalyst composition has been treated to exhibit peaks at X-ray diffraction angles (2θ) of 22.1°, 28.2°, 36.2°, 45.2°, and 50.0°.

The present invention also provides a method for increasing the yield of one or more (amm)oxidation products produced by a single-step catalytic vapor phase (amm) oxidation reaction of one or more $C_2$-$C_8$ alkanes, using one or more reaction zones, each of which comprises at least one catalyst capable of catalyzing the single-step vapor phase (amm)oxidation reaction. The inventive method comprises the steps of feeding one or more $C_2$-$C_8$ alkanes to at least one of the one or more reaction zones; and feeding carbon dioxide to at least one of the one or more reaction zones simultaneously with the feeding of the one or more $C_2$-$C_8$ alkanes.

BRIEF DESCRIPTION OF THE DRAWINGS

FIG. 1 provides a graphical representation of results achieved by the process of the present invention, at various temperatures.

DETAILED DESCRIPTION OF THE INVENTION

The present invention provides an improved single-step catalytic vapor phase (amm)oxidation process for the conversion of one or more $C_2$-$C_8$ alkanes to one or more oxidation products, including unsaturated carboxylic acids and unsaturated nitriles, whereby a higher yield of the oxidation products is achieved.

Generally, suitable starting materials for the single-step (amm)oxidation process of the present invention include, but are not limited to, one or more $C_2$ to $C_8$ alkanes, or a mixture of one or more $C_2$ to $C_8$ alkanes with one or more corresponding $C_2$ to $C_8$ alkanes, and carbon dioxide and, optionally, ammonia. Suitable starting materials may also, optionally, include an oxygen-containing gas, steam, and diluting gases.

As used herein, the term "one or more $C_2$ to $C_8$ alkanes" means one or more straight chain or branched chain alkanes having from 2 to 8 carbons atoms per alkane molecule, for example, ethane, propane, butane, pentane, heptane and octane. The term "one or more $C_2$ to $C_8$ alkenes" means one or more straight chain or branched chain alkenes having from 2 to 8 carbons atoms per alkene molecule, for example, ethene, propene, butane, pentane, heptene and octene. As used herein, the term "a mixture of one or more $C_2$ to $C_8$ alkanes with one or more corresponding $C_2$ to $C_8$ alkanes" means a mixture that includes one or more straight chain or branched chain alkanes having from 2 to 8 carbons atoms per alkane molecule and one or more of the corresponding straight chain or branched chain alkenes having from 2 to 8 carbons atoms per alkene molecule, such as, without limitation, a mixture of ethane and ethene, or a mixture of propane and propene, or a mixture of n-butane and n-butene, etc.

The particular one or more $C_2$ to $C_8$ alkanes selected as the starting materials for use in connection with the present invention will, of course, depend upon the particular desired (amm)oxidation product or products. For example, when propane or isobutane is used as the starting material alkane, acrylic acid or methacrylic acid will be obtained, respectively, in good yield.

The purity of the one or more $C_2$ to $C_8$ alkanes used as the starting material is not particularly limited, and one or more $C_2$ to $C_8$ alkanes containing a lower alkane such as methane or ethane, air or carbon dioxide, as impurities, may be used without any particular problem. Further, the starting material alkane(s) may be a mixture of various alkanes. Similarly, where a mixture of one or more $C_2$ to $C_8$ alkanes with one or more corresponding $C_2$ to $C_8$ alkanes is used as the starting material, the purity of the starting material mixture is not particularly limited, and a mixture of alkane and alkene containing a lower alkene such as ethene, a lower alkane such as methane or ethane, air or carbon dioxide, as impurities, may be used without any particular problem. Further, the starting material mixture may be a mixture of various alkanes and alkenes.

There is no limitation on the source of the one or more $C_2$ to $C_8$ alkanes. They may be purchased, per se, or in admixture with an alkene and/or other impurities. Moreover, the one or more $C_2$ to $C_8$ alkanes, regardless of source, and the one or more $C_2$ to $C_8$ alkenes, regardless of source, may be blended as desired. For example, without limitation, in a mixture of one or more $C_2$ to $C_8$ alkanes with one or more corresponding $C_2$ to $C_8$ alkanes, the one or more corresponding $C_2$ to $C_8$ alkanes may be present in an amount of at least 0.5% by weight, including at least 1.0% by weight to 95% by weight; or even 3% by weight to 90% by weight.

Similarly, there is no limitation on the source of the carbon dioxide, which may be purchased and fed to the process as fresh feed, or mixed with the one or more $C_2$ to $C_8$ alkanes, or the mixture of one or more $C_2$ to $C_8$ alkanes with one or more corresponding $C_2$ to $C_8$ alkanes. Additionally, all or a portion of the carbon dioxide fed to the (amm)oxidation process of the present invention may be recycled from downstream units of the (amm)oxidation process, or it may be obtained from other related or unrelated processes.

Turning now in more specific detail to a first embodiment of the present invention, a single-step catalytic vapor phase oxidation process is provided for producing an unsaturated carboxylic acid by feeding one or more $C_2$-$C_8$ alkanes and carbon dioxide to at least one of one or more reaction zones each of which includes at least one suitable catalyst. Suitable catalysts are those which are capable of catalyzing the single-step oxidation reaction and include, but are not limited to, the catalysts disclosed in any one of the following patent documents, each of which is hereby incorporated herein by reference: U.S. Pat. Nos. 6,383,978, 6,403,525, 6,407,031, 6,407,280, 6,461,996, 6,472,552, 6,504,053, 6,589,907, 6,624,111, 6,642,174 and 6,646,158.

More particularly, in accordance with the present invention, one or more reaction zones are provided and each reaction zone comprises at least one suitable catalyst. The one or more $C_2$-$C_8$ alkanes and carbon dioxide are each fed, at least partially simultaneously, to at least one of the one or more reaction zones, where they come into contact with the catalyst or catalysts. The one or more $C_2$-$C_8$ alkanes may be fed separately and independently from the carbon dioxide, as separate feed streams, or they may be at least partially blended with one another prior to feeding them to at least one of the one or more reaction zones. Moreover, the one or more $C_2$-$C_8$ alkanes may be fed to more than one reaction zone and such reaction zones need not be contiguous or adjacent with one another. Similarly, the carbon dioxide may be fed to more than one reaction zone and such reaction zones need not be contiguous or adjacent with one another.

Where the one or more $C_2$-$C_8$ alkanes are fed separately from the carbon dioxide, they may be fed to one or more same reaction zones, or to one or more different reaction zones. For example, in an embodiment where a total of three reaction zones arranged in series with one another are provided, the one or more $C_2$-$C_8$ alkanes could be fed to the first and last (i.e., third) reaction zones, while the carbon dioxide is fed only to the middle (i.e., second) reaction zone. Alternatively, the one or more $C_2$-$C_8$ alkanes could be fed to the first and last reaction zones, and the carbon dioxide could be fed to the first and second reaction zones, or only to the first reaction zone. Of course, there are many variations concerning the number and arrangement of reaction zones, as well as to which zones the one or more $C_2$-$C_8$ alkanes and carbon dioxide may be fed, either together or separately. All such variations are within the ability of persons having ordinary skill in the art to develop and each such variation is within the contemplation and scope of the present invention.

In the production of unsaturated carboxylic acids from one or more $C_2$-$C_8$ alkanes, it is useful to employ a starting material gas that contains steam. In such a case, as a starting material gas to be supplied to the reaction system, a gas mixture comprising a steam-containing $C_2$-$C_8$ alkane, or a steam-containing mixture of one or more $C_2$ to $C_8$ alkanes with one or more corresponding $C_2$ to $C_8$ alkenes, and an oxygen-containing gas, is often used. However, the aforesaid steam-containing alkane, or the aforesaid steam-containing mixture of alkane and alkene, and the oxygen-containing gas may be alternately (i.e., separately) supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene): (oxygen): (diluting gas): ($H_2O$) in the starting material gas is preferably (1): (0.1 to 10): (0 to 20): (0.2 to 70), more preferably (1): (1 to 5.0): (0 to 10): (5 to 40).

When steam is supplied together with the one or more $C_2$-$C_8$ alkanes, or the mixture of one or more $C_2$ to $C_8$ alkanes with one or more corresponding $C_2$ to $C_8$ alkanes, as starting material gas, the selectivity for an unsaturated carboxylic acid is distinctly improved, and the unsaturated carboxylic acid can be obtained from the one or more $C_2$-$C_8$ alkanes, or the mixture of one or more $C_2$ to $C_8$ alkanes with one or more corresponding $C_2$ to $C_8$ alkanes, as starting material gas, in good yield simply by contacting in one reaction zone (i.e., in one stage). However, the conventional technique utilizes a diluting gas, such as nitrogen, argon or helium, for the purpose of diluting the starting material. Such a diluting gas may be used together with the steam to adjust various process operating parameters, including but not limited to, the space velocity, the oxygen partial pressure and the steam partial pressure.

The detailed mechanism of the oxidation reaction of the first embodiment of the present invention is not clearly understood, but the oxidation reaction is carried out by oxygen atoms present in the one or more catalysts in each of the one or more reaction zones, or by molecular oxygen present in the feed gas. To incorporate molecular oxygen into the feed gas, such molecular oxygen may be pure oxygen gas. However, it is usually more economical to use an oxygen-containing gas such as air, since purity is not particularly required. The term "oxygen-containing gas," as used herein, refers to any gas comprising from 0.01% up to 100% oxygen, including, for example, air.

For example, the proportion of the starting materials fed to each of one or more reaction zones may be as follows: one or more $C_2$-$C_8$ alkanes, or the mixture of one or more $C_2$ to $C_8$ alkanes with one or more corresponding $C_2$ to $C_8$ alkanes, in an amount between 3 vol % and 50 vol %, such as between 7 vol % and 25 vol %; carbon dioxide in an amount between 5 vol % and 60 vol %, such as between 10 vol % and 50 vol %; oxygen in an amount between 1 vol % and 50 vol %, such as between 5 vol % and 25 vol %; and water (steam) in an amount between 1 vol % and 50 vol %, such as 5 vol % and 25 vol %, based upon the total volume of the starting materials fed to each of the one or more reaction zones. It is noted that the compositions and proportion of the starting materials fed to each of the one or more reaction zones need not be the same as one another in order to realize the benefits of the present invention and, in fact, may need to be different from one another, as will be readily understood and determinable by persons of ordinary skill in the art.

It is also possible to use only the one or more $C_2$-$C_8$ alkanes, or the mixture of one or more $C_2$ to $C_8$ alkanes with one or more corresponding $C_2$ to $C_8$ alkanes, and carbon dioxide, substantially in the absence of molecular oxygen for the vapor phase catalytic reaction. In such a case, it is preferred to adopt a catalyst regeneration method wherein at least a portion of the one or more catalysts of each reaction zone is appropriately withdrawn from each reaction zone from time to time, then sent to an oxidation regenerator, regenerated and then returned to the reaction zone for reuse. For example, the catalyst regeneration may comprise contacting an oxidative gas such as oxygen, air or nitrogen monoxide with the catalyst in the regenerator usually at a temperature of from 300° to 600° C.

A particular aspect of the first embodiment of the present invention will now be described, in still further detail, wherein acrylic acid is produced using propane (as the $C_2$-$C_8$ alkane), carbon dioxide and air (as the oxygen-containing gas). The reaction system apparatus may preferably comprise a fixed bed catalytic reactor system. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other $C_2$-$C_8$ alkanes, such as isobutane, or to mixtures of $C_2$-$C_8$ alkanes with corresponding $C_2$-$C_8$ alkenes, such as propane and propene, the composition of the feed gas may be selected in accordance with the conditions for propane.

Typical reaction conditions known to persons of ordinary skill in the art for the oxidation of propane, or isobutene, to acrylic acid, or methacrylic acid, respectively, may be utilized in the practice of the present invention. The process may be practiced in a single pass mode (only fresh feed is fed to the reactor) or in a recycle mode (at least a portion of the reactor effluent is returned to the reactor).

General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 0.2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the one or more reaction zones.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning of the oxidation products becomes less of a problem, which enables the attainment of higher selectivity to the desired products. The catalysts suitable for use with the present invention typically operate more efficiently at the lower temperature range set forth above, significantly reducing the formation of acetic acid and carbon oxides as by-products, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

Turning now in more specific detail to a second embodiment of the present invention, a single-step catalytic vapor phase ammoxidation process is provided for producing an unsaturated nitrile by feeding one or more $C_2$-$C_8$ alkanes, carbon dioxide, and ammonia to at least one of one or more reaction zones each of which includes at least one suitable catalyst. Suitable catalysts are those which are capable of catalyzing the single-step ammoxidation reaction and include, but are not limited to, the catalysts disclosed in any one of the aforementioned patent documents listed in the above description of the first embodiment of the present invention.

More particularly, in the second embodiment, one or more reaction zones are provided and each reaction zone comprises at least one suitable catalyst. The one or more $C_2$-$C_8$ alkanes, carbon dioxide, and ammonia are each fed, at least partially simultaneously, to at least one of the one or more reaction zones, where they come into contact with the catalyst or catalysts. The one or more $C_2$-$C_8$ alkanes, carbon dioxide, and ammonia may be fed separately and independently from one another, as separate feed streams, or they may be at least partially blended with one another prior to feeding them to at least one of the one or more reaction zones. In addition, any two of these three starting materials may be at least partially combined with one another before being fed to at least one of the one or more reaction zones, while the third is fed separately. Moreover, the one or more $C_2$-$C_8$ alkanes may be fed to more than one reaction zone and such reaction zones need not be contiguous or adjacent with one another. Similarly, the carbon dioxide and the ammonia may each be fed to more than one reaction zone and such reaction zones need not be contiguous or adjacent with one another.

Where the one or more $C_2$-$C_8$ alkanes, the carbon dioxide and the ammonia are fed to the reaction zones separately from one another, they may be fed to one or more same reaction zones, or to one or more different reaction zones. For example, in an embodiment where a total of three reaction zones arranged in series with one another are provided, the one or more $C_2$-$C_8$ alkanes could be fed to the first and last (i.e., third) reaction zones, while the carbon dioxide is fed only to the middle (i.e., second) reaction zone and the ammonia fed only to the first reaction zone. Alternatively, the one or more $C_2$-$C_8$ alkanes could be fed to the first and last reaction zones, and the carbon dioxide could be fed to the first and second reaction zones, or only to the first reaction zone, and the ammonia fed to the first reaction zone. Of course, there are many variations concerning the number and arrangement of reaction zones, as well as to which zones the one or more $C_2$-$C_8$ alkanes, carbon dioxide, and ammonia may be fed, either together in various combinations, or separately. All such variations are within the ability of persons having ordinary skill in the art to develop and each such variation is within the contemplation and scope of the present invention.

In the production of such an unsaturated nitrile, as the starting material alkane, it is preferred to employ a $C_{2-8}$ alkane such as ethane, propane, butane, isobutane, pentane, hexane or heptane. However, in view of the industrial application of nitriles to be produced, it is particularly beneficial to employ a lower alkane having 3 or 4 carbon atoms, particularly propane or isobutane.

Similarly, as the starting material mixture of one or more $C_{2-8}$ alkanes with one or more corresponding $C_{2-8}$ alkenes, it is preferred to employ a mixture of a $C_{2-8}$ alkane with a corresponding $C_{2-8}$ alkene, such as, without limitation, a mixture of ethane and ethene, propane and propene, butane and butene, isobutane and isobutene, pentane and pentene, hexane and hexene, and heptane and heptene. However, in view of the industrial application of nitriles to be produced, it is particularly beneficial to employ a mixture of a lower alkane having 3 or 4 carbon atoms and a corresponding lower alkene having 3 or 4 carbon atoms, such as, without limitation, propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

As with the first embodiment of the present invention, the purity of the starting material $C_{2-8}$ alkane is not particularly limited, and a $C_{2-8}$ alkane containing a lower alkane such as methane or ethane, air or carbon dioxide, as impurities, may be used without any particular problem. Further, the starting material $C_{2-8}$ alkane may be a mixture of various alkanes. Similarly, the purity of the starting material mixture of one or more $C_{2-8}$ alkanes with one or more corresponding $C_{2-8}$ alkenes is not particularly limited, and a mixture of one or more $C_{2-8}$ alkanes with one or more corresponding $C_{2-8}$ alkenes which contains a lower alkene such as ethene, a lower alkane such as methane or ethane, air or carbon dioxide, as impurities, may be used without any particular problem. Further, the starting material mixture of one or more $C_{2-8}$ alkanes with one or more corresponding $C_{2-8}$ alkenes may be a mixture of various alkanes and alkenes.

There is no limitation on the source of the one or more $C_{2-8}$ alkanes or the one or more corresponding $C_{2-8}$ alkenes. They may be purchased, per se, or in admixture with other alkanes and/or other impurities. Alternatively, they can be obtained for other related or unrelated proceses. Moreover, the one or more $C_{2-8}$ alkane, regardless of source, and the one or more $C_{2-8}$ alkene, regardless of source, may be blended together as desired.

The detailed mechanism of the ammoxidation reaction of this aspect of the present invention is not clearly understood. However, the oxidation reaction is conducted by the oxygen atoms present in the one or more catalysts in each of the one or more reaction zones, or by molecular oxygen in the feed gas. When molecular oxygen is incorporated in the feed gas, the oxygen may be pure oxygen gas. However, since high purity is not required, it is usually economical to use an oxygen-containing gas such as air. The term "oxygen-containing gas," as used herein, refers to any gas comprising from 0.01% up to 100% oxygen, including, for example, air.

For example, the proportion of the starting materials fed to each of one or more reaction zones may be as follows: one or more $C_2$-$C_8$ alkanes, or the mixture of one or more $C_2$ to $C_8$ alkanes with one or more corresponding $C_2$ to $C_8$ alkanes, in an amount between 3 vol % and 50 vol %, such as between 7 vol % and 25 vol %; carbon dioxide in an amount between 5 vol % and 60 vol %, such as between 10 vol % and 50 vol %; ammonia in an amount between 3 vol % and 50 vol %, such as between 7 vol % and 25 vol %; oxygen in an amount between 1 vol % and 50 vol %, such as between 5 vol % and 25 vol %; and water (steam) in an amount between 1 vol % and 50 vol %, such as 5 vol % and 25 vol %, based upon the total volume of the particular feed stream. It is noted that the compositions and proportion of the starting materials fed to each of the one or more reaction zones need not be the same as one another in order to realize the benefits of the present invention and, in fact, may need to be different from one another, as will be readily understood and determinable by persons of ordinary skill in the art.

As the feed gas, it is possible to use a gas mixture comprising one or more a $C_{2-8}$ alkanes, or a mixture of one or more a $C_{2-8}$ alkanes with one or more corresponding one or more a $C_{2-8}$ alkenes, ammonia and an oxygen-containing gas. However, a gas mixture comprising one or more a $C_{2-8}$ alkanes, or a mixture of one or more a $C_{2-8}$ alkanes with one or more corresponding one or more a $C_{2-8}$ alkenes, and ammonia, and an oxygen-containing gas may be supplied alternately.

When the gas phase catalytic reaction is conducted using one or more $C_2$ to $C_8$ alkanes, or a mixture of one or more $C_2$ to $C_8$ alkanes with one or more corresponding $C_2$ to $C_8$ alkenes, carbon dioxide, and ammonia substantially free from molecular oxygen, as the feed gas, it is advisable to employ a catalyst regeneration method. In such a case, at least a portion of the one or more catalysts of each reaction zone is appropriately withdrawn from each reaction zone from time to time, then sent to an oxidation regenerator, regenerated and then returned to the reaction zone for reuse. For example, the catalyst regeneration may comprise contacting an oxidative gas such as oxygen, air or nitrogen monoxide with the catalyst in the regenerator usually at a temperature of from 3000 to 600° C.

The second embodiment of the present invention will now be described in further detail with respect to a particular aspect wherein acrylonitrile is produced using propane (as the $C_2$-$C_8$ alkane), carbon dioxide, ammonia, and air (as the oxygen-containing gas). The reaction system apparatus may preferably comprise a fixed bed catalytic reactor system. The proportion of air to be supplied for the ammoxidation reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other $C_2$-$C_8$ alkanes, such as isobutane, or to mixtures of $C_2$-$C_8$ alkanes with corresponding $C_2$-$C_8$ alkenes, such as propane and propene, the composition of the feed gas may be selected in accordance with the conditions for propane.

The process of this aspect of the second embodiment of the present invention may be conducted at a temperature of, for example, from 250° C. to 480° C., such as, for example, from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

EXAMPLES

Conversion of propane to acrylic acid by single-step catalytic vapor phase oxidation was performed utilizing varying amounts of carbon dioxide in the starting materials, from 0 vol % to 50 vol %, in 10% increments, and at varying temperatures between 365° C. to 390° C., in increments of 5° C. The amount of propane in the starting materials was kept constant at 9.2 vol % and the amount of oxygen in the starting materials was kept constant at 19.1 vol %, based upon the total volume of the starting materials fed to the reaction zones, with the balance comprising argon as a diluting gas. All processes were operated at atmospheric pressure (i.e., 1 atmosphere).

Each of the examples was performed in an experimental reactor system using a three-zone tube reactor configuration at normal and vacuum conditions. This reaction system comprised three basic components: a valve manifold, a reactor and a mass spectrometer. The mass spectrometer is contained in a high-vacuum system that can easily accommodate low-intensity fast transient response experiments, and can handle high volume continuous flows as a result of a specially designed slide valve that permits the reactor to operate at vacuum or high pressure conditions ($10^{-8}$ to 7000 torr).

The reactor tube length was 33 millimeters ("mm") and its diameter was 5 mm. The three reaction zones included two inert zones, each of 12 mm in length and packed with 730 mg of quartz particles, and a one catalyst zone, positioned between the inert zones. The catalyst zone was 3.3 mm in length and packed with 120 mg of a suitable catalyst.

The starting material gas mixtures of propane, oxygen, $CO_2$, and argon were passed through a fritted, heated water bubbler (at 65° C.) before being admitted to the reactor through a continuous flow valve at 1 atmosphere. Additional reaction conditions included a contact time of 3.3 seconds, and at each catalyst bed temperature, the heating rates were varied from 0.5° C./minute to 20° C./minute.

For each process example, the reactor was evacuated to $10^{-6}$ torr and small reactant or product gas pulses ($10^{13}$ molecules/pulse) were passed over the catalyst. The outlet (i.e., product) composition measurements were performed by passing a small portion of the outlet flow into the mass spectrometer chamber through a needle valve located between the reactor exit and a vacuum chamber.

The catalyst used in the examples was prepared in a manner similar to the synthesis procedure disclosed in U.S. Pat. No. 6,642,174. More particularly, a catalyst of nominal composition $Mo_{1.0}V_{0.3}Te_{0.23}Nb_{0.17}O_x$ was prepared in the presence of nitric acid in the following manner: 200 mL of an aqueous solution containing ammonium heptamolybdate tetrahydrate (1.0 M Mo), ammonium metavanadate (0.3 M V) and telluric acid (0.23M Te) formed by dissolving the corresponding salts in water at 70° C., was added to a 2000 mL rotavap flask. Then 200 mL of an aqueous solution of ammonium niobium oxalate (0.17 M Nb), oxalic acid (0.155 M) and nitric acid (0.24 M) were added thereto. After removing the water via a rotary evaporator with a warm water bath at 50° C. and 28 mm Hg, the solid materials were further dried in a vacuum oven at 25° C. overnight and then calcined.

Calcination was effected by placing the solid materials in an air atmosphere and then heating them to 275° C. at 10° C./min and holding them under the air atmosphere at 275° C. for one hour; the atmosphere was then changed to argon and the material was heated from 275° C. to 600° C. at 2° C./min and the material was held under the argon atmosphere at 600° C. for two hours. XRD analysis revealed diffraction peaks at the following angles (±0.3°) of 2θ: 22.1°, 36.2°, 45.2° and 50.0°.

Example Set A

The reaction temperature was held constant at about 365° C. and the amount of carbon dioxide was varied from 0 vol % to 50 vol %, in 10 vol % increments. The results are shown in Table 1 below and the graph provided in FIG. 1.

Example Set B

The reaction temperature was held constant at about 370° C. and the amount of carbon dioxide was varied from 20 vol % to 50 vol %, in 10 vol % increments. The results are shown in Table 1 below and the graph provided in FIG. 1.

Example Set C

The reaction temperature was held constant at about 375° C. and the amount of carbon dioxide was varied from 0 vol % to 50 vol %, in 10 vol % increments. The results are shown in Table 1 below and the graph provided in FIG. 1.

Example Set D

The reaction temperature was held constant at about 380° C. and the amount of carbon dioxide was varied from 0 vol % to 50 vol %, in 10 vol % increments. The results are shown in Table 1 below and the graph provided in FIG. 1.

Example Set E

The reaction temperature was held constant at about 385° C. and the amount of carbon dioxide was varied from 0 vol % to 50 vol %, in 10 vol % increments. The results are shown in Table 1 below and the graph provided in FIG. 1.

Example Set F

The reaction temperature was held constant at about 390° C. and the amount of carbon dioxide was varied from 0 vol % to 50 vol %, in 10 vol % increments. The results are shown in Table 1 below and the graph provided in FIG. 1.

TABLE 1

| | Acrylic Acid Yield (%) | | | | | |
|---|---|---|---|---|---|---|
| % $CO_2$ in Feed | Set A (365° C.) | Set B (370° C.) | Set C (375° C.) | Set D (380° C.) | Set E (385° C.) | Set F (390° C.) |
| 0 | 20.8 | | 22.2 | 22.6 | 23.4 | 24.3 |
| 10 | 20.9 | | 22.5 | 23.1 | | |
| 20 | 21.5 | 22.1 | 23.9 | 24.3 | 24.7 | 25.3 |
| 30 | 21.9 | 22.5 | 23.7 | 24.3 | 24.7 | 25.3 |
| 40 | 22.7 | 23.1 | 24.1 | 24.9 | 25.5 | 25.6 |
| 50 | 22.1 | 22.9 | 23.8 | 24.9 | 25.8 | 26.4 |

With reference to the graph provided in FIG. 1, it is noted that, since the carbon dioxide content was zero for the first data point for each Example Set (except for Set B), this point is the comparative example at each of the six operating temperatures tested. The remaining data points represent various applications of the present invention and show that, at a given temperature, increased acrylic acid yield can be achieved by increasing the amount of carbon dioxide feed to the oxidation process.

We claim:

1. A process for single-step catalytic vapor phase (amm)oxidation of one or more $C_2$-$C_8$ alkanes to produce one or more (amm)oxidation products selected from the group consisting of unsaturated carboxylic acids and unsaturated nitriles, wherein one or more reaction zones are provided, each of which comprises at least one catalyst capable of catalyzing the single-step vapor phase (amm)oxidation reaction, said process comprising the steps of:
  (a) feeding the one or more $C_2$-$C_8$ alkanes to at least one of the one or more reaction zones; and
  (b) feeding carbon dioxide, in an amount of from 5 volume % to 60 volume %, based upon the total volume of starting materials that are fed to said process, to at least one of the one or more reaction zones simultaneously with the feeding of the one or more $C_2$-$C_8$ alkanes, wherein the at least one catalyst comprises a mixed metal oxide having the empirical formula:

$$J_jM_mN_nY_yZ_zO_o$$

wherein J is at least one element selected from the group consisting of Mo and W,
  M is at least one element selected from the group consisting of V and Ce,
  N is at least one element selected from the group consisting of Te, Sb and Se,
  Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements; and
  wherein said catalyst composition has been treated to exhibit peaks at X-ray diffraction angles (2θ) of 22.1°, 28.2°, 36.2°, 45.2°, and 50.0°.

2. The process of claim 1, wherein the one or more $C_2$-$C_8$ alkanes are fed in an amount of from 3 volume % to 50 volume %, based upon the total volume of starting materials that are fed to said process.

3. The process of claim 1, wherein a feed stream comprising the one or more $C_2$-$C_8$ alkanes and another feed stream comprising carbon dioxide are combined prior to feeding to the one or more reaction zones.

4. The process of claim 1, wherein a first feed stream comprising the one or more $C_2$-$C_8$ alkanes and a second feed stream comprising carbon dioxide are fed independently of one another to the one or more reaction zones.

5. The process of claim 4, wherein said first feed stream comprising the one or more $C_2$-$C_8$ alkanes is fed to at least one of the one or more reaction zones and said second feed stream comprising carbon dioxide is fed to the same at least one of the one or more reaction zones to which said first feed stream is fed.

6. The process of claim 4, wherein said first feed stream comprising the one or more $C_2$-$C_8$ alkanes is fed to at least one of the one or more reaction zones and said second feed stream comprising carbon dioxide is fed to a different at least one of the one or more reaction zones to which said first feed stream is fed.

7. The process of claim 1, further comprising the step of feeding an oxygen-containing gas to the one or more reaction zones simultaneously with the feeding of the one or more $C_2$-$C_8$ alkanes.

8. The process of claim 7, wherein the one or more $C_2$-$C_8$ alkanes comprise at least propane and the one or more (amm)oxidation products comprise at least (meth)acrylic acid.

9. The process of claim 1, further comprising the step of feeding ammonia to the one or more reaction zones simultaneously with the feeding of the one or more $C_2$-$C_8$ alkanes.

10. The process of claim 9, wherein the one or more $C_2$-$C_8$ alkanes comprise at least propane and the one or more (amm)oxidation products comprise at least acrylonitrile.

11. A method for increasing the yield of one or more (amm)oxidation products selected from the group consisting of unsaturated carboxylic acids and unsaturated nitriles and produced by a single-step catalytic vapor phase (amm)oxidation reaction of one or more $C_2$-$C_8$ alkanes, wherein one or more reaction zones are provided, each of which comprises at least one catalyst capable of catalyzing the single-step vapor phase (amm)oxidation reaction, said method comprising the steps of:
  (a) feeding one or more $C_2$-$C_8$ alkanes to at least one of the one or more reaction zones; and
  (b) feeding carbon dioxide, in an amount of from 5 volume % to 60 volume %, based upon the total volume of starting materials that are fed to said process, to at least one of the one or more reaction zones simultaneously with the feeding of the one or more $C_2$-$C_8$ alkanes, wherein the at least one catalyst comprises a mixed metal oxide having the empirical formula:

$$J_jM_mN_nY_yZ_zO_o$$

wherein J is at least one element selected from the group consisting of Mo and W,
  M is at least one element selected from the group consisting of V and Ce,
  N is at least one element selected from the group consisting of Te, Sb and Se,
  Y is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu, and Z is selected from the group consisting of Ni, Pd, Cu, Ag and Au; and wherein, when j=1, m=0.01 to 1.0, n=0.01 to 1.0, y=0.01 to 1.0, z=0.001 to 0.1 and o is dependent on the oxidation state of the other elements; and
  wherein said catalyst composition has been treated to exhibit peaks at X-ray diffraction angles (2θ) of 22.1°, 28.2°, 36.2°, 45.2°, and 50.0°.

* * * * *